Figure 1:
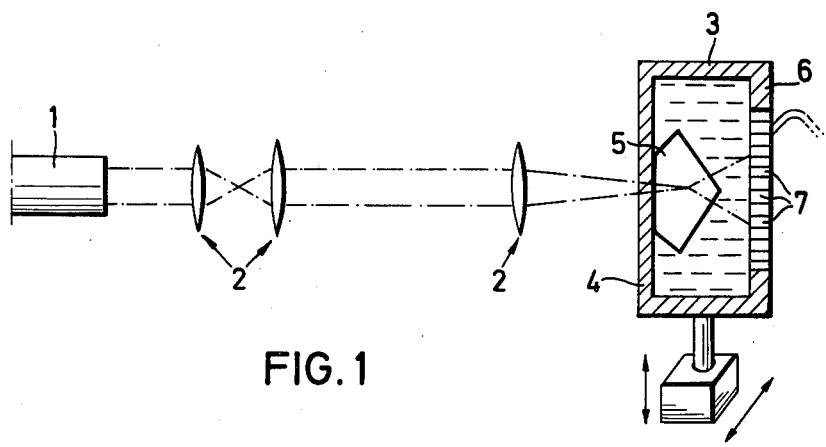

United States Patent [19]

Bruck

[11] 4,152,069
[45] * May 1, 1979

[54] PROCESS AND APPARATUS FOR ASCERTAINMENT OF THE VALUATION DATA OF GEMS

[75] Inventor: Gernot K. Bruck, Cologne, Fed. Rep. of Germany

[73] Assignee: Dihaco/Diamanten Handels Compagnie, Mauren, Liechtenstein

[ * ] Notice: The portion of the term of this patent subsequent to Sep. 20, 1994, has been disclaimed.

[21] Appl. No.: 765,562

[22] Filed: Feb. 4, 1977

[30] Foreign Application Priority Data

Feb. 5, 1976 [DE] Fed. Rep. of Germany ....... 2604410
May 26, 1976 [DE] Fed. Rep. of Germany ....... 2623595

[51] Int. Cl.² ............................................. G01N 21/32
[52] U.S. Cl. ........................................ 356/30; 356/239
[58] Field of Search ................... 356/30, 31, 200, 239

[56] References Cited

U.S. PATENT DOCUMENTS

| 2,960,909 | 11/1960 | Shipley | 356/30 |
| 3,867,032 | 2/1975 | Bruck | 356/30 |
| 4,049,350 | 9/1977 | Bruck | 356/30 |

*Primary Examiner*—John K. Corbin
*Assistant Examiner*—R. A. Rosenberger
*Attorney, Agent, or Firm*—Jones, Thomas & Askew

[57] ABSTRACT

Process and apparatus for determining the presence and location of inclusions within gems. A gem is initially scanned or irradiated along X and Y co-ordinates by a light bundle whose cross-section perpendicular to the scanning tracks is at least equal to the spacing between adjacent tracks. The intensity of light passing through the gem is measured to determine the possible existence of any inclusions. The gem and the source of light are next moved relative to each other along the Z co-ordinate, so that the focal point of the light rays moves within the gem to pinpoint the location of any inclusions therein.

19 Claims, 4 Drawing Figures

FIG.3
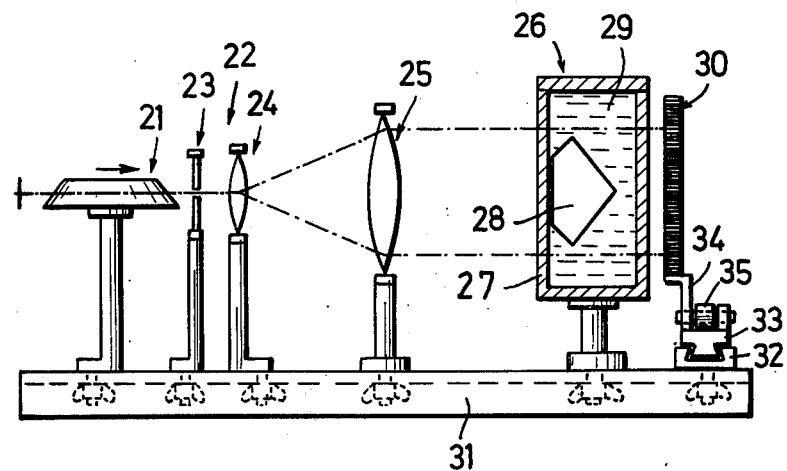
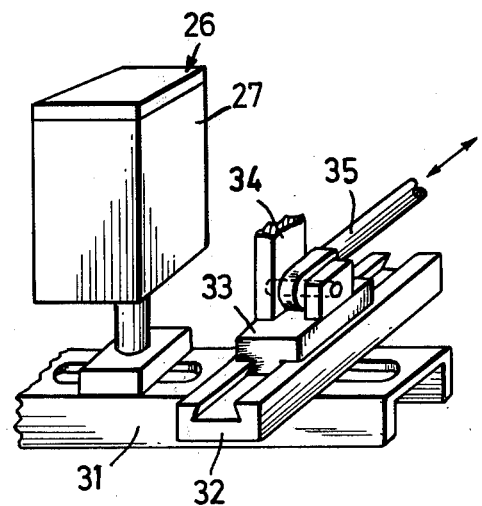
FIG.4

PROCESS AND APPARATUS FOR ASCERTAINMENT OF THE VALUATION DATA OF GEMS

The present invention relates to a process for ascertainment of the valuation data of gems, wherein the respectively examined gem is scanned by a narrowly bundled light bundle, the bundle cross-section of which lies in the order of mangitude of the smallest inclusions to be ascertained, over its entire plane of cross-section perpendicular to the incident light bundle along scanning tracks, the mutual spacing of which is at most equal to the cross-section of the bundle, and the intensity of the light bundle is measured after it is influenced by the examined gem.

By this already proposed process, the inclusions disposed in the gem can be ascertained in their position, for example with reference to the plane of the pane of the gem. When this plane of the pane is laid for example into an X-Y co-ordinate system, then the respective X and Y co-ordinates of the inclusions can be determined by this process. Thereagainst, the spatial location of the inclusions is not detected by this process, which means expressed with reference to a usual three-dimensional X, Y and Z co-ordinate system that the respective Z co-ordinate is not stated with the aid of this process. Just this additional statement is however of importance for an unambiguous characterisation of the gem.

The present invention is therefore based on the task of augmenting the initially described process in the sense that, in addition to the X and Y co-ordinates of the inclusions, also their respective Z co-ordinate can be determined. According to the invention, this is attained thereby, that consecutive to the process for the determination of the X and Y co-ordinates, strongly spread light rays, running parallel and impinging on the gem, are focussed in such a manner that their focal point falls into the gem to be examined and the focal point of the rays is displaced in a direction perpendicular to the plane of cross-section to the co-ordinate of the plane of cross-section of the respectively ascertained inclusion and the intensity of the light emerging from the gem is measured.

Thus, according to the invention, the X and Y co-ordinates of the inclusions in the gem are intially ascertained and subsequently the spatial depth of the inclusions is measured within these measured co-ordinates. In that case, the invention utilizes the recognition that it is possible to spread or enlarge the parallel rays, emitted particularly by a laser, of a ray bundle with a bundle diameter of 0.3 to 1 millimeter and subsequently to focus it so that only such inclusions, which fall directly into the focal point, bring about a relevant light intensity change. In that case, a focussing ensues which is the stronger, the greater is the spreading. The measure of the spreading is thus decisive for the possibility of focussing.

According to the invention, it can be expedient when the displacing of the focal point ensues by continuous reciprocation of at least one lens system in a direction perpendicular to the plane of cross-section. According to the invention, it is just as possible to perform the displacing of the focal point by a continuous reciprocation of the gem in a direction perpendicular to the plane of cross-section. In that case, the amplitude of the reciprocation of the gem or of the focussing lens starting from a zero position is each time the measure for the position of the inclusion in the direction perpendicular to the plane of cross-section, as soon as the focal point of the rays co-incides with the inclusion and thus an impairment of the emerging light intensity is recorded, namely in comparison to the light intensity of the emerging light as long as the focal point of the rays does not fall into the range of an inclusion.

The present invention furthermore relates to a process for the ascertainment of the valuation data of coloured gems, especially cut diamonds, wherein the gem to be examined is irradiated perpendicularly over its entire plane of cross-section lying perpendicularly to the incident light and the light rays emerging from the gem and evaluated.

In this case, the task now exists of making possible a rapid throughput of stones without difficult adjusting measures, and namely in connection with a simple construction. According to the invention, this is attained thereby, that the static gem is irradiated by a ray bundle consisting of parallel rays and the rays emerging from the gem are detected in raster fashion for evaluation. It is thus the shadow of possible gem inclusions that is detected without the stone or the ray optical system having to be particularly adjusted or moved for this. The measurement accuracy rather more depends in essence upon the resolution in raster fashion. In that case, the measurement accuracy is the greater, the smaller is the resolving raster. By laying the raster plane into a plane of, for example, X and Y co-ordinates, the position of the respective inclusion in this plane can be determined exactly. For this, the center of the gem is expediently aligned previously to the center of the co-ordinate plane.

According to the invention, it can furthermore be expedient when irradiation is by monochromatic rays and at least one ray running externally of the gem is compared in its spectrum with at least one ray running preferably centrally through the gem. Hereby, a simultaneous colour determination of the gem is possible, so that an objective statement about the colour and the colour intensity of the gem is obtained. The spectral comparison can for example ensue with a standard spectral curve.

In advantageous refinement of the aforementioned process, the gem to be examined can be irradiated in a state fully submerged in an immersion liquid. In that case, it is furthermore of advantage, when the refractive index of the immersion liquid is approximated as far as possible to the refractive index of the gem for the wavelength of the incident light. In the case of the examination of diamonds, it is expedient to choose the refractive index of the immersion liquid between 2 and 2.4. According to the invention, the refractive index of the immersion liquid should amount to at least 2.2. By reason of this process step according to the invention, it is attained that no constant background noise is recorded in the measurement of the light intensity influenced by the gem to be examined, but the maximum signal, since the light can pass through the gem practically unhindered in the interference-free case, i.e. when no inclusions are present. Since the gem to be examined is fully submerged in the strongly refractive liquid, wherein the refractive index of the liquid is as far as possible approximated to that of the gem, the reflection problems on the transition of the light bundle from the liquid into the gem are practically avoided. The light bundle can thus pass through unhindered through the gem itself in the edge region thereof up to the equipment measuring the intensity. Only when the light bundle impinges upon an inclusion, is it scattered and the intensity reduction recorded.

According to the invention, it is furthermore of advantage when the examined gem is scanned or irradiated with its pane facing the incident light and the light bundle is a laser ray bundle.

Figure 2:
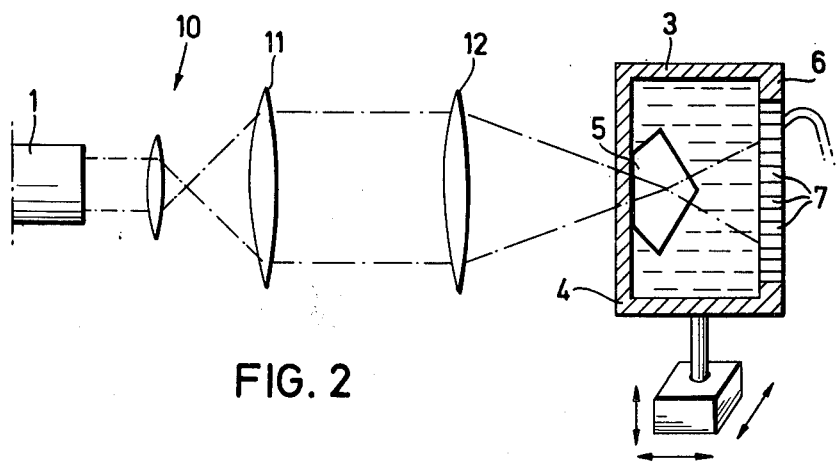

The invention is more closely explained with reference to the examples of embodiment illustrated in the accompanying drawings. There show:

FIG. 1 a basic view of an apparatus for the detection of inclusions in the X-Y co-ordinate plane, FIG. 2 an apparatus for the performance of the process according to the invention, FIG. 3 a partly sectioned side elevation of another apparatus according to the invention and FIG. 4 a partial view of the apparatus according to FIG. 3.

As is evident from FIG. 1, an apparatus for performance of the process for detection of the inclusions in respect of their X and Y co-ordinates comprises a light force 1, for example a laser or a luminescent diode, a lens system 2 and a container 3. A gem 5 is arranged in the container 3 with its pane parallel to the front container wall 4. A light-sensitive equipment 7, for example built up of individual photo-cells, is provided at the rear wall 6 of the container 3. The extent in area of the light-sensitive equipment 7 in the rear wall is so chosen that even the largest stones to be examined can be arranged with their projection area on the rear wall within this light-sensitive equipment. Disposed within the container 3 is an immersion liquid 8 with a refractive index matched to the refractive index of the gem 5. The gem 5 adheres at the inside of the front wall 5 by reason of the adhesion arising between the two contact areas. The lens system 2 is in that case dimensioned in such a manner that the light ray of the light bundle emerging from it and running through the gem possesses a cross-section corresponding to the order of magnitude of the smallest inclusions to be ascertained.

It is now possible with the aid of a drive, not illustrated in the drawing, of the container 3 to move the container in such a scanning track that the incident light bundle and the gem respectively to be examined during the scanning are displaced relative to one another along a strip-shaped or a meander-shaped track, so that the gem is scanned along parallel planes of cross-section.

The equipment illustrated in FIG. 2 serves for the performance of the process according to the invention, wherein also here again a light source 1 of a laser of a luminescent diode is present. However, the lens system 10, by difference from the lens system 2 according to FIG. 1, is dimensioned in such a manner that the parallel rays are at first strongly spread in at least one enlarging lens 11 and then focussed in at least one collecting lens 12, so that they intersect in a focal point lying in a gem 5 to be examined. The lenses possess a special permeability and coating for laser light so that about 100% permeability is obtained. The container 3, which corresponds to the container 3 according to FIG. 1, is here however still displaceable in and against the ray direction so that the focal point of the rays can be displaced continuously within the gem. Should the focal point now fall upon an inclusion in the gem, a weakening of the light energy emerging at the container rear wall and falling on the light-sensitive equipment is recorded by this and recorded in the form of intensity interruptions, for example in a connected, not illustrated recording device. By reason of the setting of the container proceeding from a zero position, which co-incides with the position of the focal point for example in the plane of the pane of the gem 5, the spatial position of the inclusion can now be ascertained exactly after the position thereof in the X-Y plane has been detected with the aid of the equipment according to FIG. 1. The not illustrated displacing equipment for the container 3 in or against the ray direction can for example be in the manner of a micrometer screw. In that case, the drive can ensue by hand or by motor. Just the same, the focussing lens 12 can also be arranged to be displaceable.

A further equipment for ascertainment of the valuation data of a coloured gem consists for example of a light source 21, which is constructed as continuously tunable dye laser, as well as of a lens system 22, consisting of a diaphragm 23, an enlarging lens 24 and a collecting lens 25, wherein spread parallel rays emanate from the latter. Arranged in their ray course is a container 26, in which a gem 28 is arranged with its pane parallel to the front container wall 27. Disposed within the container 26 is an immersion liquid 29 with a refractive index matched to the refractive index of the gem 28, wherein the liquid is as transparent as possible in the entire visible range. The gem 28 adheres at the inside of the front wall 27 by reason of the adhesion arising between the two contact areas. Arranged directly behind the container is a photocell matrix 30, which preferably possesses a raster up to 1000×1000 so that a resolving capacity of 0.01 millimeters is attained. The dimensions of the photocell matrix are expediently matched to the size of the container, so that even with the largest gems to be measured, rays running outside the gems can still be received, so that a reference measurement can likewise ensue for colour measurement between the rays running externally and the rays running for example centrally through the gem.

The entire measuring equipment is attached to a common base strip 31, namely each individual part displaceable and adjustable on its own. As is furthermore evident, the photocell matrix is likewise displaceable on a rail 32 running perpendicularly to the base strip 31 and crossing this. This is expedient when the photocell matrix consists of one line of photocells, in order then to travel over the entire width of the stone by continuous displacement. This displacement expediently takes place by motor, for which a carriage 33, on which the photocell matrix 30 is attached by an angle bracket 34, can be driven to and fro continuously in a dovetail guide through a push rod 35 by a not illustrated motor on the rail 32.

I claim:

1. Process for ascertainment of the valuation data of gems by determining the possible presence and location of any inclusions in the gem, wherein the respectively examined gem is initially scanned by a narrowly bundled light bundle, the bundle cross-section of which lies in the order of magnitude of the smallest inclusions to be ascertained over its entire plane of cross-section perpendicular to the incident light bundle along scanning tracks, the spacing between adjacent scanning tracks being at most equal to the cross-section of the bundle, and the intensity of the light bundle is measured after it is influenced by the examined gem, characterised thereby, that subsequent to said initial scanning, strongly spread light rays, running parallel and impinging on the gem, are focussed in such a manner that their focal point falls into the gem to be examined and the focal point of the rays is displaced in a direction perpendicular to the plane of cross-section to the co-ordinates of the plane of cross-section of the respectively ascertained inclusion, and the intensity of the light emerging from the gem is measured.

2. Process according to claim 1, characterised thereby, that the displacement of the focal point ensues by continuous reciprocation of the gem in a direction perpendicular to the plane of cross-section.

3. Process according to claim 1, characterised thereby, that the displacement of the focal point ensues by a continuous reciprocation of at least one lens system in a direction perpendicular to the plane of cross-section.

4. Apparatus for the ascertainment and determination of size of inclusion in gems for performance of the process according to claim 1, consisting of a container, in which the respective gem to be examined is insertable in a preselected alignment and into which is filled an immersion liquid reaching beyond the uppermost point of the gem, a light source with lens systems which delivers a light bundle with a bundle cross-section in the order of magnitude of the smallest inclusions to be ascertained, a setting device, by which the light bundle is alignable at a preselected solid angle to the gem inserted in the container, and a moving device which moves the gem and the light bundle relative to one another along a preselected scanning track, characterised thereby, that the first lens system is exchangeable against a second lens system (11, 12), which generates a spread and subsequently focussed course of light rays with a focal point in the gem (5), and the container (3) containing the gem (5) or the lens system (11, 12) is mounted to be displaceable in and against a direction perpendicular to the plane of cross-section.

5. Apparatus according to claim 4, characterised thereby, that the light source (1) consists of a laser or a luminescent diode and the second following lens system consists of at least one enlarging lens (11) and at least one following collecting lens (12).

6. Apparatus according to claim 4, characterised thereby, that a light-sensitive equipment (7), measuring the intensity of the light bundle that has passed through the gem (5) to be examined, is arranged on the side of the gem (5) remote from the light bundle.

7. Apparatus according to claim 6, characterised thereby, that the light-sensitive equipment (7) displays an extent in area which is at least equal to the extent of the largest plane of cross-section lying parallel to it of the gem (5) to be examined.

8. Process for ascertainment of the valuation data of coloured gems, especially cut diamonds, wherein the gem to be examined is irradiated perpendicularly over its entire plane of cross-section lying perpendicularly to the incident light and the light rays emerging from the gem are evaluated, characterised thereby, that the static gem is irradiated by a ray bundle consisting of parallel rays and the rays emerging from the gem are detected in raster fashion for evaluation.

9. Process according to claim 8, characterised thereby, that irradiation is by monochromatic rays and at least one ray running externally of the gem is compared in its spectrum with at least one ray running preferably centrally through the gem.

10. Process according to claim 8, characterised thereby, that the gem respectively to be examined is scanned or irradiated while it is fully submerged in an immersion liquid and that the intensity of the light bundle passing through the gem is detected.

11. Process according to claim 10, characterised thereby, that the refractive index of the immersion liquid is as closely as possible approximated to the refractive index of the gem for the wave length of the incident light bundle.

12. Process according to claim 11, characterised thereby, that the refractive index of the immersion liquid in the examination of diamonds lies between 2 and 2.4.

13. Process according to claim 12, characterised thereby, that the refractive index of the immersion liquid amounts to at least 2.2.

14. Process according to claim 8, characterised thereby, that the examined gem is scanned with its pane aligned at right angles to the axis of the bundle and facing the incident light bundle.

15. Process according to claim 8, characterised thereby, that the light bundle is a laser ray bundle.

16. Apparatus for performance of the process according to claim 8, characterised by continuously tunable laser for the generation of monochromatic light, a lens system (22) arranged therebehind in the direction for spreading and generating a ray bundle of parallel rays, a container (26) arranged in the ray course thereof, into which the gem (28) is insertable in preselected alignment and an immersion liquid (29) is filled reaching beyond the uppermost point of the gem, and a photocell matrix (30) arranged behind the container (26).

17. Apparatus according to claim 16, characterised thereby, that the photocell matrix (30) possesses a raster of 1000×1000.

18. Apparatus according to claim 17, characterised thereby, that the photocell matrix (30) displays an extent in area which is at least equal to and preferably greater than the extent of the largest plane of cross-section lying parallel to it of the gem to be examined.

19. Apparatus according to claim 16, characterised thereby, that the photocell matrix (30) consists of a line of photocells, which is arranged to be displaceable at the rearside of the container (26) perpendicularly to the ray direction.

* * * * *